US011980338B2

(12) United States Patent
Chen (10) Patent No.: US 11,980,338 B2
(45) Date of Patent: May 14, 2024

(54) ENDOSCOPE DEVICE

(71) Applicant: Chicony Electronics Co., Ltd., New Taipei (TW)

(72) Inventor: Hsin-Hung Chen, New Taipei (TW)

(73) Assignee: CHICONY ELECTRONICS CO., LTD., New Taipei (TW)

(*) Notice: Subject to any disclaimer, the term of this patent is extended or adjusted under 35 U.S.C. 154(b) by 97 days.

(21) Appl. No.: 17/244,143

(22) Filed: Apr. 29, 2021

(65) Prior Publication Data

US 2022/0142455 A1    May 12, 2022

(30) Foreign Application Priority Data

Nov. 11, 2020  (TW) ................................. 109139408

(51) Int. Cl.
*A61B 1/00* (2006.01)
*A61B 1/04* (2006.01)
(Continued)

(52) U.S. Cl.
CPC ...... *A61B 1/00073* (2013.01); *A61B 1/00009* (2013.01); *A61B 1/00066* (2013.01);
(Continued)

(58) Field of Classification Search
CPC ............ A61B 1/00009; A61B 1/00066; A61B 1/00071; A61B 1/00073; A61B 1/00096;
(Continued)

(56) References Cited

U.S. PATENT DOCUMENTS 11,744,449 B2 * 9/2023 Loo ...................... H05K 1/0203
600/158
2007/0173695 A1 * 7/2007 Hirata ................ G02B 23/2461
600/152
(Continued)

FOREIGN PATENT DOCUMENTS

CN        210990141 U      7/2020
CN        211408967 U      9/2020
(Continued)

*Primary Examiner* — John P Leubecker
(74) *Attorney, Agent, or Firm* — Muncy, Geissler, Olds & Lowe, P.C.

(57) ABSTRACT

An endoscope device includes a hollow tube, a thermal-conductive member, an image-capturing module, and a heat-dissipation tube. The hollow tube includes an insertion end. The thermal-conductive member is in the hollow tube and adjacent to the insertion end. The thermal-conductive member includes a first end, a second end, and a receiving groove. The first end is near to the insertion end as compared with the second end, and the receiving groove is between the first end and the second end. The image-capturing module includes a camera module and a circuit board in the receiving groove. The camera module is at the insertion end and electrically connected to the circuit board. The first end contacts the camera module. The heat-dissipation tube is in the hollow tube. One end of the heat-dissipation tube contacts the thermal conductive member, and the other end of the heat-dissipation tube extends away from the insertion end.

16 Claims, 9 Drawing Sheets (51) Int. Cl.
*A61B 1/06* (2006.01)
*A61B 1/12* (2006.01)

(52) U.S. Cl.
CPC .......... *A61B 1/00124* (2013.01); *A61B 1/042* (2013.01); *A61B 1/0661* (2013.01); *A61B 1/128* (2013.01)

(58) Field of Classification Search
CPC ... A61B 1/00114; A61B 1/00124; A61B 1/05; A61B 1/128
See application file for complete search history.

(56) References Cited

U.S. PATENT DOCUMENTS

| | | | |
|---|---|---|---|
| 2008/0151046 A1* | 6/2008 | Scott | |
| 2008/0158349 A1* | 7/2008 | Miller | H04N 5/2256 348/82 |
| 2008/0300457 A1* | 12/2008 | Hosaka | A61B 1/00096 600/110 |
| 2009/0315986 A1* | 12/2009 | Ohara | A61B 1/05 348/E7.085 |
| 2011/0313252 A1* | 12/2011 | Lin | A61B 1/00105 361/679.01 |
| 2012/0209072 A1 | 8/2012 | Que et al. | |
| 2013/0077257 A1* | 3/2013 | Tsai | H04N 5/2253 361/720 |
| 2013/0137925 A1* | 5/2013 | Ushijima | |
| 2014/0168507 A1* | 6/2014 | Renaud | H04N 5/2253 348/373 |
| 2016/0000309 A1* | 1/2016 | Weber | A61B 1/12 600/179 |
| 2016/0028926 A1* | 1/2016 | Ichimura | H05K 1/0201 348/68 |
| 2016/0278620 A1* | 9/2016 | Kawayoke | G02B 23/2492 |
| 2019/0056583 A1 | 2/2019 | Kuhn et al. | |
| 2020/0333581 A1* | 10/2020 | Kobayashi | G02B 23/2423 |
| 2021/0345868 A1* | 11/2021 | Fu | |
| 2022/0095904 A1* | 3/2022 | Chen | A61B 1/00103 |

FOREIGN PATENT DOCUMENTS

| | | |
|---|---|---|
| JP | 6259583 B2 * | 1/2018 |
| TW | M547945 U | 3/2017 |
| TW | M602016 U | 10/2020 |

* cited by examiner

ENDOSCOPE DEVICE

CROSS-REFERENCE TO RELATED APPLICATION

This non-provisional application claims priority under 35 U.S.C. § 119(a) to Patent Application No. 109139408 filed in Taiwan, R.O.C. on Nov. 11, 2020, the entire contents of which are hereby incorporated by reference.

BACKGROUND

Technical Field

The instant disclosure relates to an image capturing device, in particular, to an endoscope device.

Related Art

Endoscope is a technology widely used in industries and medical fields. With the insertion of the endoscope into the human body, the doctor can observer the status of the organ of the patient through the image capturing module of the endoscope device. hence, the doctor can diagnose the body of the patient.

SUMMARY

However, during the use of the endoscope, operations of the electronic components insides the endoscope (e.g., the image capturing module, the light source, or the circuit board) may generate heats, thereby causing the temperature of the inserted portion of the endoscope device to increase continuously thus the endoscope device cannot be provided for a long-time use. Moreover, when the temperature of the endoscope device is too high, the human body may be hurt easily and the electronic component may be damaged easily.

In view of this, in one embodiment, an endoscope device is provided. The endoscope device comprises a hollow tube, a thermal conductive member, an image capturing module, and a heat dissipation tube. The hollow tube comprises an insertion end. The thermal conductive member is disposed in the hollow tube and adjacent to the insertion end. The thermal conductive member comprises a first end, a second end, and a receiving groove. The first end is near to the insertion end as compared with the second end, and the receiving groove is located between the first end and the second end. The image capturing module comprises a camera module and a circuit board. The circuit board is received in the receiving groove. The camera module is disposed at the insertion end and electrically connected to the circuit board. The first end of the thermal conductive member contacts the camera module. The heat dissipation tube is disposed in the hollow tube. One of two ends of the heat dissipation tube contacts the thermal conductive member, and the other end of the heat dissipation tube extends away from the insertion end.

As above, according to the endoscope device of one or some embodiments of the instant disclosure, the thermal conductive member contacts the camera module and is provided for assembling and contacting the circuit board and the heat dissipation tube. Hence, the heat generated by operations of the camera module and the circuit board can be transmitted through the thermal conductive member and the heat dissipation tube, thus preventing from the condition that the human body is hurt by the excessive temperature of the inserted portion of the endoscope device, increasing the operation time of the endoscope device, and increasing lifetime of the electronic components in the endoscope device.

BRIEF DESCRIPTION OF THE DRAWINGS

The disclosure will become more fully understood from the detailed description given herein below for illustration only, and thus not limitative of the disclosure, wherein.

DETAILED DESCRIPTION

Embodiments are provided for facilitating the descriptions of the instant disclosure. However, the embodiments are provided as examples for illustrative purpose, but not a limitation to the instant disclosure. In all the figures, same reference numbers designate identical or similar elements.

Figure 1:
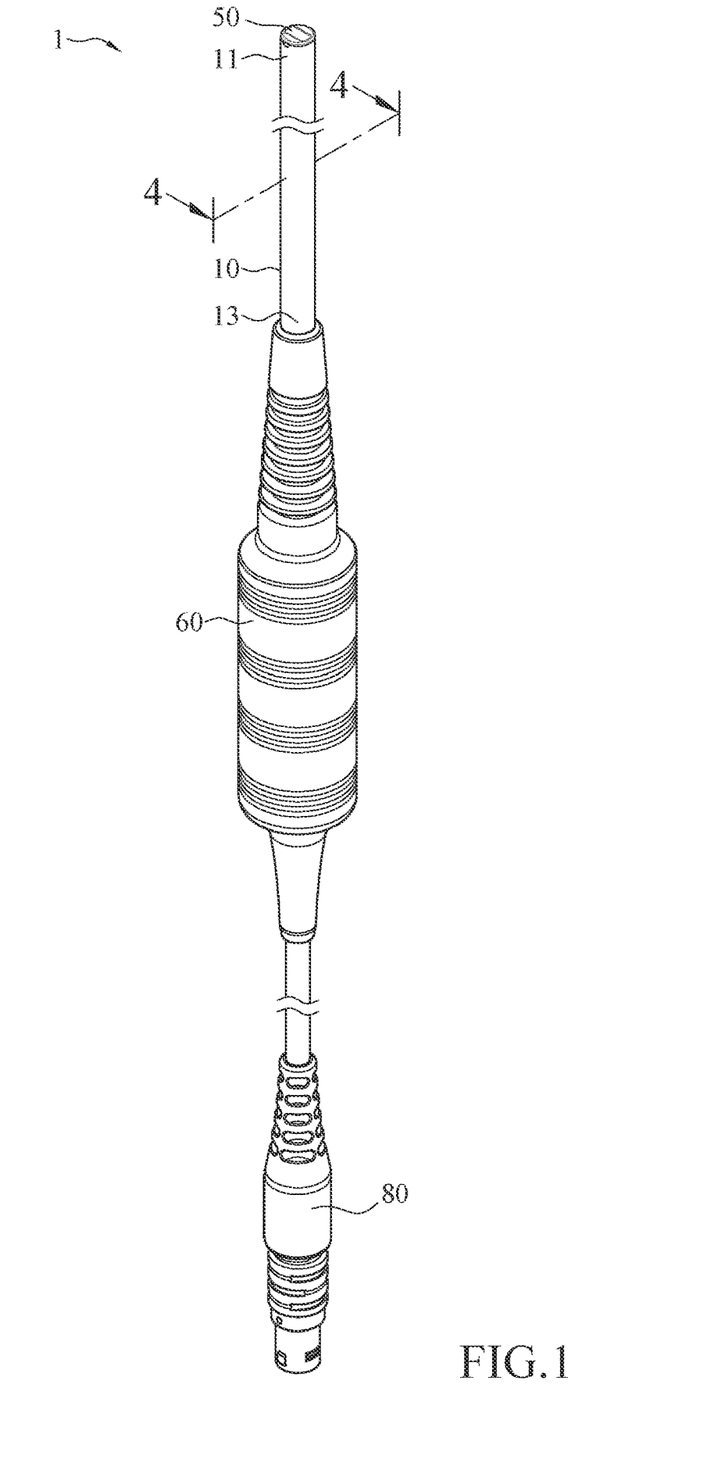
FIG. 1 illustrates a perspective view of an endoscope device according to a first embodiment of the instant disclosure.
Figure 2:
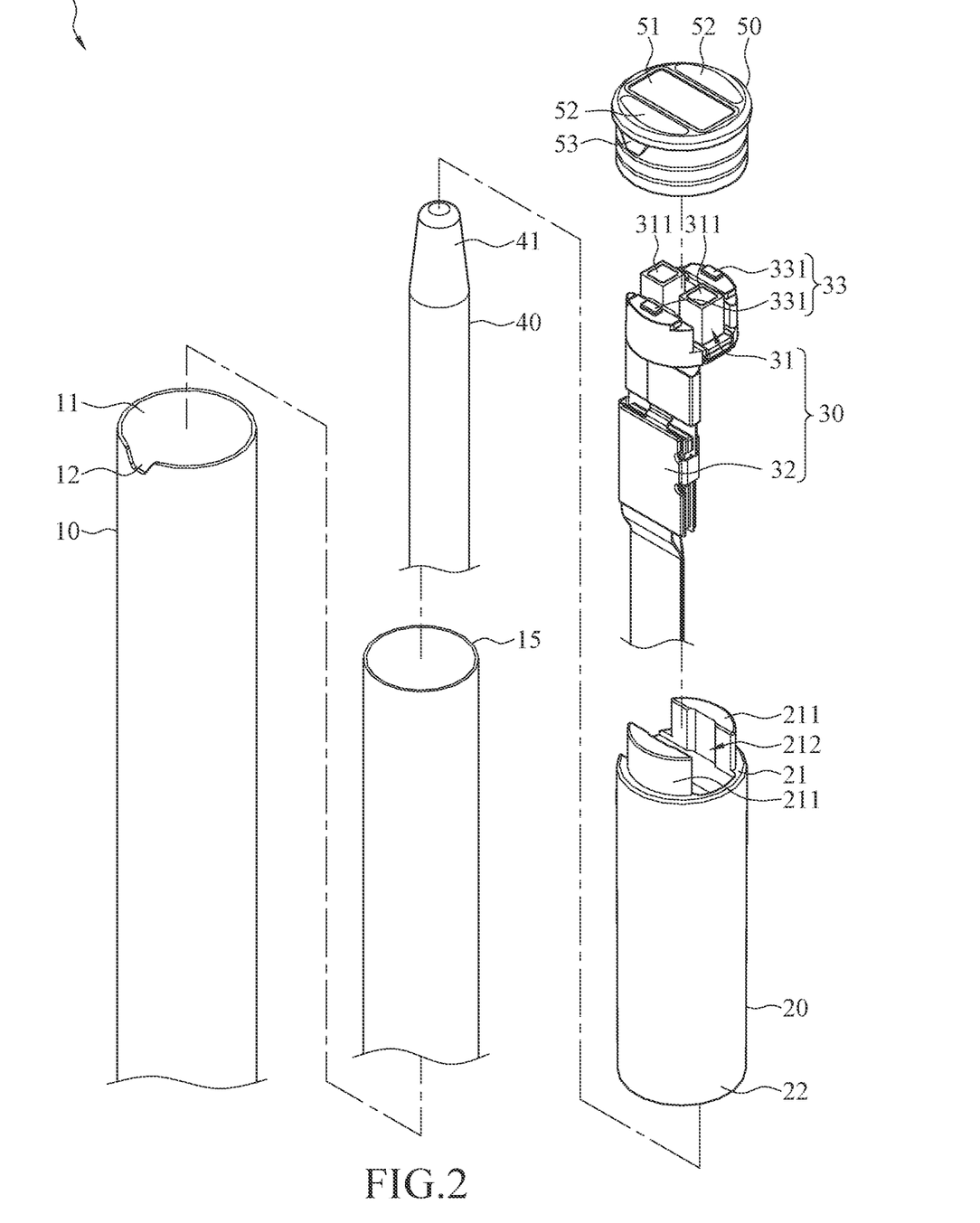
FIG. 2 illustrates an exploded view of the endoscope device of the first embodiment.
Figure 3:
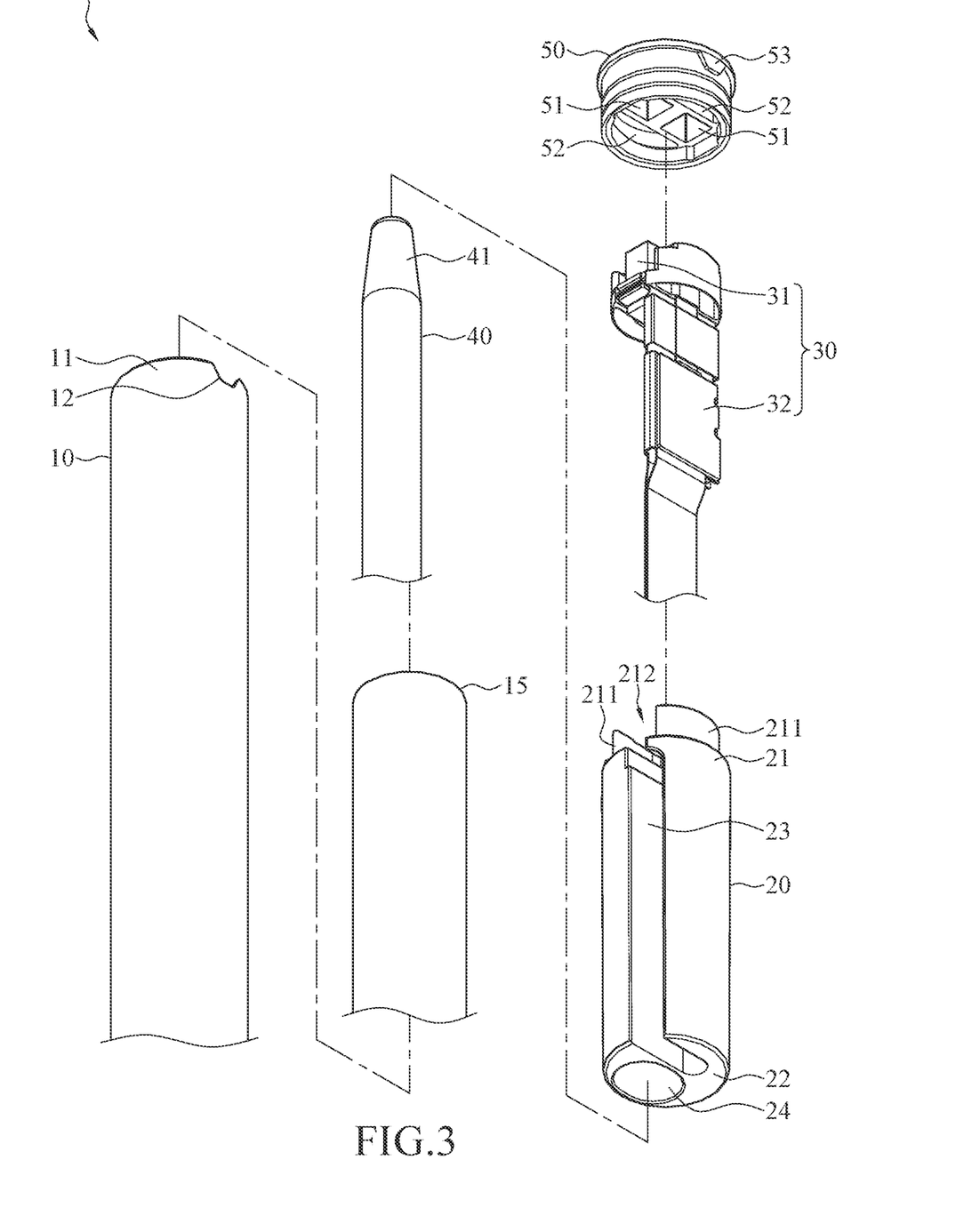
FIG. 3 illustrates another exploded view of the endoscope device of the first embodiment.
Figure 4:
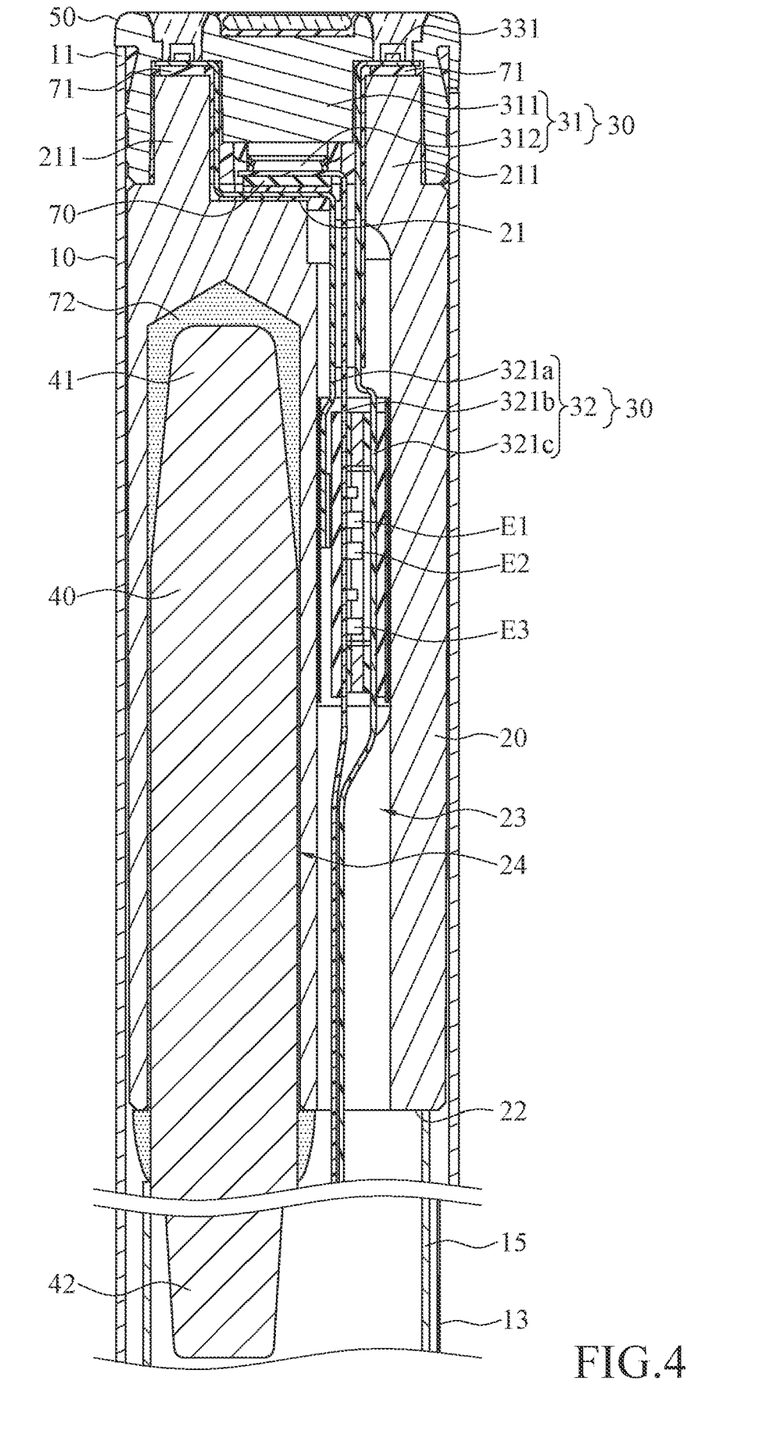
FIG. 4 illustrates a cross-sectional view along line 4-4 shown in FIG. 1.

FIG. 1 illustrates a perspective view of an endoscope device 1 according to a first embodiment of the instant disclosure. FIG. 2 illustrates an exploded view of the endoscope device 1 of the first embodiment. FIG. 3 illustrates another exploded view of the endoscope device 1 of the first embodiment. FIG. 4 illustrates a cross-sectional view along line 4-4 shown in FIG. 1. As shown in FIGS. 1 to 4, in this embodiment, the endoscope device 1 comprises a hollow tube 10, a thermal conductive member 20, an image capturing module 30, and a heat dissipation tube 40. The thermal conductive member 20, the image capturing module 30, and the heat dissipation tube 40 are disposed in the hollow tube 10.

As shown in FIGS. 1 to 4, the hollow tube 10 may be a rigid tube or a flexible tube. For example, the hollow tube 10 may be a rigid plastic-type material tube (e.g., a plastic tube or a rubber tube), a metal tube (e.g., an iron tube, a stainless tube, a copper tube, an aluminum tube, or an alloy tube), a glass tube, or may be tubes with great thermal conductivity. Alternatively, the hollow tube 10 may be a composite tube (e.g., the hollow tube 10 may be a composite tube made of at least two materials from plastics, rubbers, and metals).

As shown in FIGS. 1 to 4, the hollow tube 10 comprises an insertion end 11 and an operation end 13 opposite to the insertion end 11. The image capturing module 30 comprises a camera module 31 and a circuit board 32. The camera module 31 is disposed at the insertion end 11 and electrically connected to the circuit board 32. The user can insert the insertion end 11 of the hollow tube 10 into the human body. Therefore, the image inside the human body can be captured or the condition inside the human body can be observed by the camera module 31 of the image capturing module 30. In this embodiment, the hollow tube 10 is a round tube so as to be inserted into the human body conveniently, but embodiments are not limited thereto; the hollow tube 10 may be an elliptical tube, a square tube, or tubes in other shapes.

As shown in FIGS. 1 to 4, the thermal conductive member 20 is disposed in the hollow tube 10 and adjacent to the insertion end 11. The thermal conductive member 20 comprises a first end 21, a second end 22, a receiving groove 23, and an insertion groove 24. The first end 21 is near to the insertion end 11 of the hollow tube 10 as compared with the second end 22. In other words, a distance between the first end 21 and the insertion end 11 is shorter than a distance between the second end 22 and the insertion end 11. The receiving groove 23 is located between the first end 21 and the second end 22. The insertion groove 24 is disposed at the second end 22. At least a portion of the circuit board 32 of the image capturing module 30 is received in the receiving groove 23 to contact the inner surface of the thermal conductive member 20. The first end 21 of the thermal conductive member 20 contacts the camera module 31. In some embodiments, the thermal conductive member 20 may be made of material(s) with great thermal conductivity, such as copper, aluminum, aluminum alloy, or other materials with high thermal conductivity coefficients.

As shown in FIGS. 1 to 4, in this embodiment, the thermal conductive member 20 is a post (in this embodiment, the thermal conductive member 20 is a round post, but embodiments are not limited thereto). The receiving groove 23 is recessed from one side of the thermal conductive member 20 and is in communication with the first end 21 and the second end 22. The receiving groove 23 and the insertion groove 24 are not in communication with each other. Several electronic components E1-E3 (e.g., microprocessors, resistors, capacitors, oscillators, or the like) may be provided on the circuit board 32. The electronic components E1-E3 may be located in the receiving groove 23 and indirectly contact the inner surface of the thermal conductive member 20. In this embodiment, one of two ends of the circuit board 32 extends out of the first end 21 so as to be electrically connected to the camera module 31, and the other end of the circuit board 32 extends out of the second end 22 so as to be connected to a signal output cable 80 (as shown in FIG. 1). Therefore, the image signal captured by the camera module 31 can be output outwardly through the signal output cable 80. For example, the signal output cable 80 may output the image signal to the display, so that the image can be presented on the display.

As shown in FIGS. 1 to 4, the heat dissipation tube 40 is disposed in the hollow tube 10. Moreover, one of two ends of the heat dissipation tube 40 is inserted into the insertion groove 24 to contact the thermal conductive member 20, and the other end of the heat dissipation tube 40 extends away from the insertion end 11. The other end of the heat dissipation tube 40 may extend to the operation end 13, so that the length and the heat dissipation area of the heat dissipation tube 40 can be increased to enhance the heat dissipation performance. In some embodiments, the heat dissipation tube 40 may be positioned by other ways to contact the thermal conductive member 20. For example, the heat dissipation tube 40 may be positioned to contact the thermal conductive member 20 by gluing, engaging, abutting, soldering, or the like, and the heat dissipation tube 20 is not limited to be inserted into the insertion groove 24.

Furthermore, the deeper the depth of the insertion groove 24 of the thermal conductive member 20 is, the more the contact area between the heat dissipation tube 40 and the thermal conductive member 20 is. Therefore, the thermal conduction effect can be further enhanced. As shown in FIG. 4, in this embodiment, the depth of the insertion groove 24 of the thermal conductive member 20 is greater than half of the length of the thermal conductive member 20. For example, if the length of the thermal conductive member 20 is 2 cm, the depth of the insertion groove 24 of the thermal conductive member 20 may be greater than 1 cm. Alternatively, the insertion groove 24 may be defined through the thermal conductive member 20 from the first end 21 to the second end 22, thereby further increasing the contact area between the heat dissipation tube 40 and the thermal conductive member 20.

In some embodiments, the heat dissipation tube 40 may be made of materials with great thermal conductivity, such as copper, aluminum, aluminum alloy, or other materials with high thermal conductivity coefficients. Moreover, the heat dissipation tube 40 may be a solid tube. Alternatively, the heat dissipation tube 40 may be a heat pipe and comprises a vaporization end 41 and a condensation end 42 opposite to the vaporization end 41, and the vaporization end 41 of the heat dissipation tube 40 is inserted into the insertion groove 24 of the thermal conductive member 20. For example, the heat dissipation tube 40 comprises a copper tube, a working liquid, and a capillary structure. The inner portion of the copper tube is vacuumed, and the working liquid and the capillary structure are disposed in the copper tube. When the vaporization end 41 is heated, the working liquid vaporizes into the gas phase and flows toward the condensation end 42. Then, when the gas phase working liquid flowing to the condensation end 42 is cooled, the working liquid condensates into the liquid phase and the working liquid is transmitted back to the vaporization end 41 through the capillary structure. Accordingly, the circulating endothermic operation and exothermic operation of the heat dissipation tube 40 allows the heat to be transmitted and dissipated quickly.

Accordingly, the first end 21 of the thermal conductive member 20 contacts the camera module 31, the receiving groove 23 of the thermal conductive member 20 is provided for receiving the circuit board 32 and contacts the circuit board 32, and one end of the heat dissipation tube 40 contacts the thermal conductive member 20. Therefore, when the endoscope device 1 is in use, the heat generated by operations of the camera module 31 and the electronic components E1-E3 on the circuit board 32 can be quickly transmitted to the thermal conductive member 20 and can be further dissipated through the heat dissipation tube 40, thus preventing from the condition that the human body is hurt by the excessive temperature of the inserted portion of the endoscope device 1 (e.g., the portion of the hollow tube 10 adjacent to the insertion end 11). Moreover, the camera module 31 and the circuit board 32 may be prevented from being overheated easily (e.g., temperatures of the camera module 31 and the circuit board 32 may be maintained under 35 Celsius degrees for a long time). Hence, the safety of the endoscope device 1 can be improved, thereby extending the operation time of the endoscope device 1 and increasing the lifetime of the image capturing module 30.

In some embodiments, the first end 21 of the thermal conductive member 20 may contact the camera module 31 directly or indirectly. For example, as shown in FIG. 4, in this embodiment, the first end 21 of the thermal conductive member 20 indirectly contact the camera module 31 through a thermal conductive body 70. The thermal conductive body 70 may be a thermal conductive glue or a thermal conductive paste. In this embodiment, the heat between the thermal conductive member 20 and the camera module 31 can be transmitted through the thermal conductive body 70. Moreover, the thermal conductive body 70 may be provided for positioning the thermal conductive member 20 and the camera module 31. Alternatively, the thermal conductive body 70 may be a thermal conductive sheet or a thermal conductive silicon rubber so as to be sandwiched between the first end 21 of the thermal conductive member 20 and the camera module 31, thereby preventing the condition that the manufacturing tolerance or assembly tolerance between the components causes the thermal conductive member 20 and the camera module 31 fail to contact each other. Preferably, in one embodiment, the thermal conductive body 70 may achieve both the positioning and the heat conduction effects, and it is understood that the type and the positioning manner of the thermal conductive body 70 are not limited to the foregoing embodiments.

In some embodiments, the camera module 31 comprises at least one lens 311 and at least one optical sensing element 312. As shown in FIG. 4, in this embodiment, the optical sensing element 312 of the camera module 31 is electrically connected to the circuit board 32 (e.g., the optical sensing element 312 may be electrically connected to the circuit board 32 through wires). A predetermined space is maintained between the optical sensing element 312 and the lens 311. Hence, when an external light enters into the camera module 31 from the lens 311, the light can be focused at the optical sensing element 312. The first end 21 of the thermal conductive member 20 contacts the optical sensing element 312. Therefore, during the operation of the optical sensing element 312, the heat generated by the optical sensing element 312 can be transmitted to the thermal conductive member 20. For example, as shown in FIG. 2, in this embodiment, the camera module 31 comprises two lenses 311 (e.g., a left lens and a right lens). The two lenses 311 may respectively capture a left image and a right image, so that the images can be synthesized as a three-dimensional image, but embodiments are not limited thereto. In some embodiments, the camera module 31 may comprise one lens 311. Specifically, in this embodiment, the optical sensing element 312 may be a charge-coupled device (CCD), a complementary metal-oxide semiconductor (CMOS), a CMOS active pixel sensor, a wafer-level image sensor, or the like.

As shown in FIGS. 1 to 4, in this embodiment, the image capturing module 30 further comprises a light emitting source 33. The light emitting source 33 is disposed at the insertion end 11 of the hollow tube 10 for auxiliary illumination. Hence, the image capturing module 31 can obtain clearer images through the illumination of the light emitting source 33. In this embodiment, the first end 21 of the thermal conductive member 20 further contacts the light emitting source 33. Hence, during the operation of the light emitting source 33, the heat generated by the light emitting source 33 can be quickly transmitted to the thermal conductive member 20, and the heat can be further transmitted and dissipated through heat dissipation tube 40, thus preventing from the condition that the human body is hurt by the excessive temperature of the inserted portion of the endoscope device 1. Moreover, the lifetime of the light emitting source 33 can be extended.

In some embodiments, the light emitting source 33 may be an incandescent lamp, a halogen lamp, or an LED lamp. For example, the light emitting source 33 may be an SMT (surface mounted technology) LED, so that the light emitting source 33 can be attached on the circuit board through automated machines, thereby greatly reducing labor costs and time costs.

In some embodiments, the thermal conductive member 20 may directly or indirectly contact the light emitting source 33. For example, as shown in FIG. 4, the thermal conductive member 20 indirectly contacts the light emitting source 33 through at least one thermal conductive layer 71. In this embodiment, the light emitting source 33 comprises a plurality of light emitting elements (in this embodiment, two light emitting elements 331), and the thermal conductive member 20 indirectly contacts the two light emitting elements 331 through two thermal conductive layers 71, respectively. The thermal conductive layer 71 may be a thermal conductive glue layer or a thermal conductive paste layer. In this embodiment, the heat between the thermal conductive member 20 and the light emitting source 33 can be transmitted through the thermal conductive layer 71. Moreover, the thermal conductive layer 71 may be provided for positioning the thermal conductive member 20 and the light emitting source 33. Alternatively, the thermal conductive layer 71 may be a thermal conductive sheet or a thermal conductive silicon rubber layer so as to be sandwiched between the thermal conductive member 20 and the light emitting source 33, thereby preventing the condition that the manufacturing tolerance or assembly tolerance between the components causes the thermal conductive member 20 and the light emitting source 33 fail to contact each other.

Further, as shown in FIGS. 1 to 4, in this embodiment, the first end 21 of the thermal conductive member 20 comprises two thermal conductive posts 211 and a groove 212 between the two thermal conductive posts 211. The camera module 31 corresponds to the groove 212, and the two light emitting elements 331 correspond to the two thermal conductive posts 211, respectively. Since the size of the camera module 31 is greater than the size of the light emitting source 33, the large-sized camera module 31 is received in the groove 212, and the thermal conductive member 20 contacts the two light emitting elements 2 through the end portions of the two thermal conductive posts 211, respectively. Accordingly, the thermal conduction area of the thermal conductive member 20 can be increased (since the thermal conductive member 20 further comprises the two thermal conductive posts 211 in this embodiment), and the space inside the hollow tube 10 can be utilized properly.

Further, as shown in FIG. 4, the circuit board 32 may be a flexible circuit board and comprises a plurality of flexible membrane circuit layers (in this embodiment, the circuit board comprises at least three membrane circuit layers 321a, 321b, 321c). The membrane circuit layers 321a, 321b, 321c are stacked with each other and are electrically connected to the camera module 31 and the light emitting source 33, respectively. In this embodiment, two membrane circuit layers 321a, 321c of the circuit board 32 extend out of the first end 21 of the thermal conductive member 20 and are electrically connected to the two light emitting elements 331, respectively, and the membrane circuit layer 321b extends out of the first end 21 of the thermal conductive member 20 and is electrically connected to the camera module 31. Accordingly, since the circuit board 32 is a flexible circuit board and is received in the receiving groove 23 by stacking, more wires and electronic components can be provided in the limited space inside the hollow tube 10, thereby greatly reducing the size of the endoscope device 1 and allowing the assembling of the endoscope device 1 to be more convenient.

As shown in FIGS. 1 to 4, the camera module 31 and the light emitting source 33 can be assembled at the insertion end 11 of the hollow tube 10 through a cap 50. In this embodiment, the cap 50 is assembled at the insertion end 11 of the hollow tube 10. The cap 50 comprises a central assembling opening 51 and two side assembling openings 52. The two side assembling openings 52 surround the central assembling opening 51. Preferably, in one embodiment, the camera module 31 is disposed at the central assembling opening 51, and the two light emitting elements 331 of the light emitting source 33 are respectively disposed at the two side assembling openings 52, but embodiments are not limited thereto.

As shown in FIG. 3, the cap 50 has a first aligning portion 53, the insertion end 11 of the hollow tube 10 has a second aligning portion 12, and the first aligning portion 53 may correspond to the second aligning portion 12, thereby preventing the cap 50 from being assembled with insertion end 11 of the hollow tube 10 by a wrong assembling direction which would cause the camera module 31 to capture a wrong image (e.g., the captured image may be an up-side down image). In this embodiment, the first aligning portion 53 of the cap 50 is a protrusion, and the second aligning portion 12 of the insertion end 11 of the hollow tube 10 is a notch, but embodiments are not limited thereto. The first aligning portion 53 and the second aligning portion 12 may be other structures as long as the first aligning portion 53 and the second aligning portion 12 can be assembled with each other.

Figure 5:
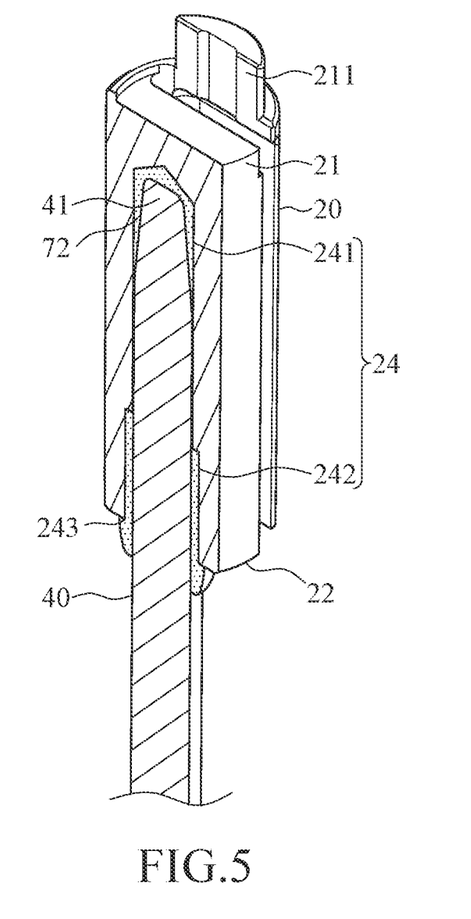
FIG. 5 illustrates a partial perspective view of the endoscope device of the first embodiment.

As shown in FIG. 5, which illustrates a partial perspective view of the endoscope device 1 of the first embodiment. In this embodiment, a thermal conductive adhering layer 72 is filled between the heat dissipation tube 40 and the insertion groove 24 of the thermal conductive member 20. For example, the thermal conductive adhering layer 72 may be a thermal conductive glue or a thermal conductive paste. The thermal conductive adhering layer 72 may have similar functions as the thermal conductive layer 71. In this embodiment, the heat between the thermal conductive member 20 and the heat dissipation tube 40 can be transmitted through the thermal conductive adhering layer 72. Moreover, the thermal conductive adhering layer 72 may be provided for positioning the thermal conductive member 20 and the heat dissipation tube 40. For example, the conductive adhering layer 72 may be silver paste glue, and for example, the silver paste glue may be formed by silver powder and a fixing glue so as to have heat transmission function and adhering function at the same time. Alternatively, the conductive adhering layer 72 may be a low-temperature solder paste, the low-temperature solder paste may be used to fix the heat dissipation tube 40 with the thermal conductive member 20. The low-temperature solder paste has a better heat conduction performance. In the embodiment that the conductive adhering layer 72 is the low-temperature solder paste, the fixing glue is not required.

Further, as shown in FIG. 5, in this embodiment, the insertion groove 24 of the thermal conductive member 20 comprises an insertion opening 243, an inner portion 241 and an outer portion 242, the outer portion 242 communicates between the inner portion 241 and insertion opening 243, a width of the inner portion 241 is less than a width of the outer portion 242, and one of two ends of the heat dissipation tube 40 is inserted into the insertion groove 24 from the insertion opening 243. Accordingly, one end of the heat dissipation tube 40 can be inserted into the insertion groove 24 in a convenient manner, thereby improving the convenience for assembling the endoscope device 1. Moreover, during the assembling procedure, the thermal conductive glue or the thermal conductive paste may be filled in the inner portion 241 in advance. Therefore, when one end of the heat dissipation tube 40 is inserted into the inner portion 241, the thermal conductive glue or the thermal conductive paste may flow to the outer portion 242 having the larger width so as to fill up the inner space of the insertion groove 24. Hence, the thermal conductive glue or the thermal conductive paste can be prevented from flowing out of the insertion groove 24.

Figure 6:
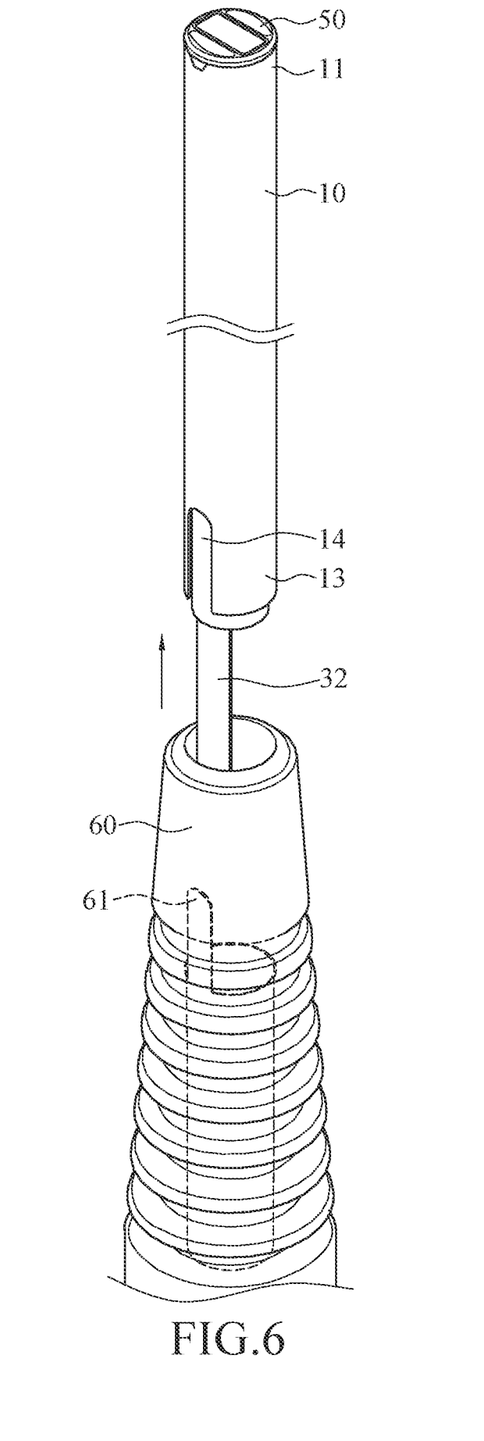
FIG. 6 illustrates yet another exploded view of the endoscope device of the first embodiment.
Figure 7:
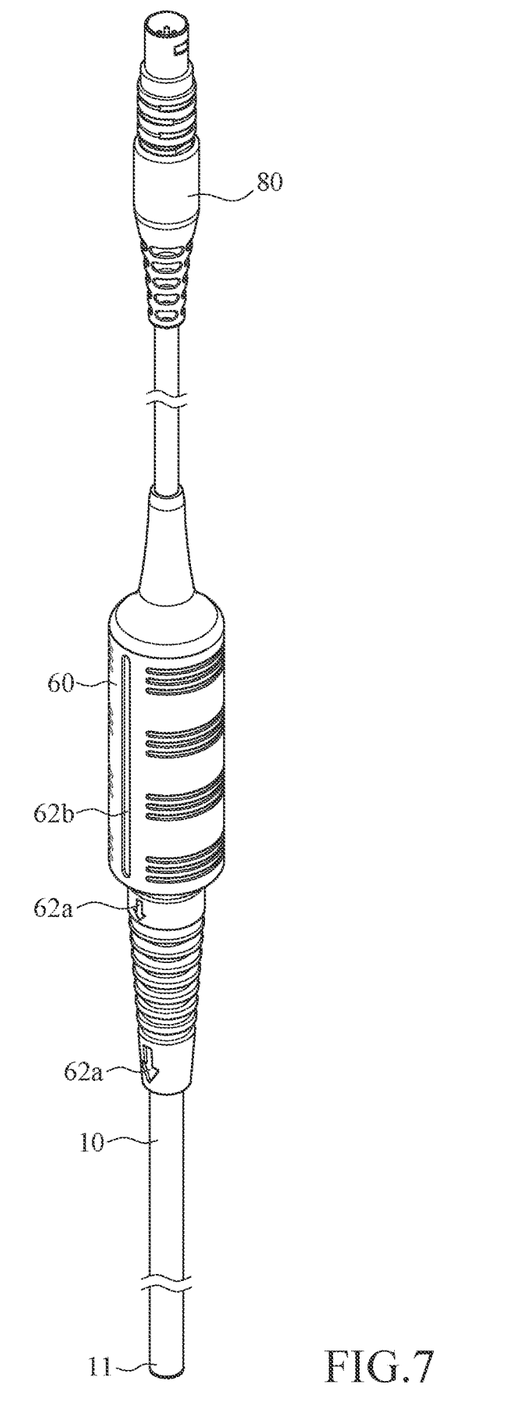
FIG. 7 illustrates another perspective view of the endoscope device of the first embodiment.

As shown in FIGS. 6 and 7, which respectively illustrate an exploded view and a perspective view of the endoscope device 1 of the first embodiment. In this embodiment, a handle 60 is further assembled with the operation end 13 of the hollow tube 10, so that the user can operate the endoscope device 1 by holding the handle 60.

As shown in FIG. 6, the handle 60 further has a first aligning member 61, the operation end 13 of the hollow tube 10 has a second aligning member 14, and the first aligning member 61 corresponds to the second aligning member 14, thereby preventing the handle 60 from being assembled with the operation end 13 of the hollow tube 10 by a wrong assembling direction and thereby improving the assembling efficiency. In this embodiment, the first aligning member 61 of the handle 60 is a block protruding from the inner surface of the handle 60, and the second aligning member 14 of the operation end 13 of the hollow tube 10 is a notch, but embodiments are not limited thereto. The first aligning member 61 and the second aligning member 14 may be other structures as long as the first aligning member 61 and the second aligning member 14 can be assembled with each other.

As shown in FIG. 7, in this embodiment, the handle 60 further comprises at least one mark portion, and the mark portion corresponds to an image capturing direction of the image capturing module 30. Accordingly, when the user operates the endoscope device 1, the user can realize the image capturing direction of the image capturing module 30 quickly through the mark portion, thereby improving the operation efficiency. In this embodiment, the handle 60 comprises three mark portions (two mark portions 62a and a mark portion 62b). In this embodiment, the mark portions 62a are arrow shaped and direct toward the insertion end 11 of the hollow tube 10 so as to indicate the image capturing direction of the image capturing module 30, but embodiments are not limited thereto. In some embodiments, the mark portion 62a may be a pattern like an indication line, an indication spot, an indication symbol, an indication figure, an indication text, or the like, and the mark portion 62a may be positioned on the surface of the handle 60 through printing, adhering, or other manners. Alternatively, the mark portion 62a may be integrally formed with the handle 60. Moreover, "the mark portion 62a corresponds to the image capturing direction of the image capturing module 30" indicates that the direction of the mark portion 62a and the image capturing direction are the same directions or are opposite directions, embodiments are not limited thereto.

Further, as shown in FIG. 7, in this embodiment, the mark portion 62b of the handle 60 is a surface texture. For example, in this embodiment, the mark portion 62b is a straight groove pattern, but embodiments are not limited thereto. In some embodiments, the mark portion 62b may be protruding pattern or groove patterns in other shapes. Similarly, the direction of the mark portion 62b and the image capturing direction may be the same direction or opposite directions. Accordingly, when the user holds the handle 60, the user can realize the image capturing direction of the image capturing module 30 through the tactile feeling of the mark portion 62b.

As shown in FIGS. 2 and 4, in this embodiment, an insulation tube 15 is further disposed in the hollow tube 10. The insulation tube 15 may be a tubular member made of insulation materials. In some embodiments, the insulation material may be inorganic insulation material (e.g., ceramic and asbestos), organic insulation materials (e.g., resin, rubber, silk, cotton, and paper), or a composite insulation material formed by the foregoing insulation materials. At least one portion of the heat dissipation tube 40 is located in the insulation tube 15, thereby preventing the heat dissipation tube 40 and the hollow tube 10 from contacting each other to affect the heat dissipation effect and also preventing the endoscope device 1 from generating static electricity.

Figure 8:
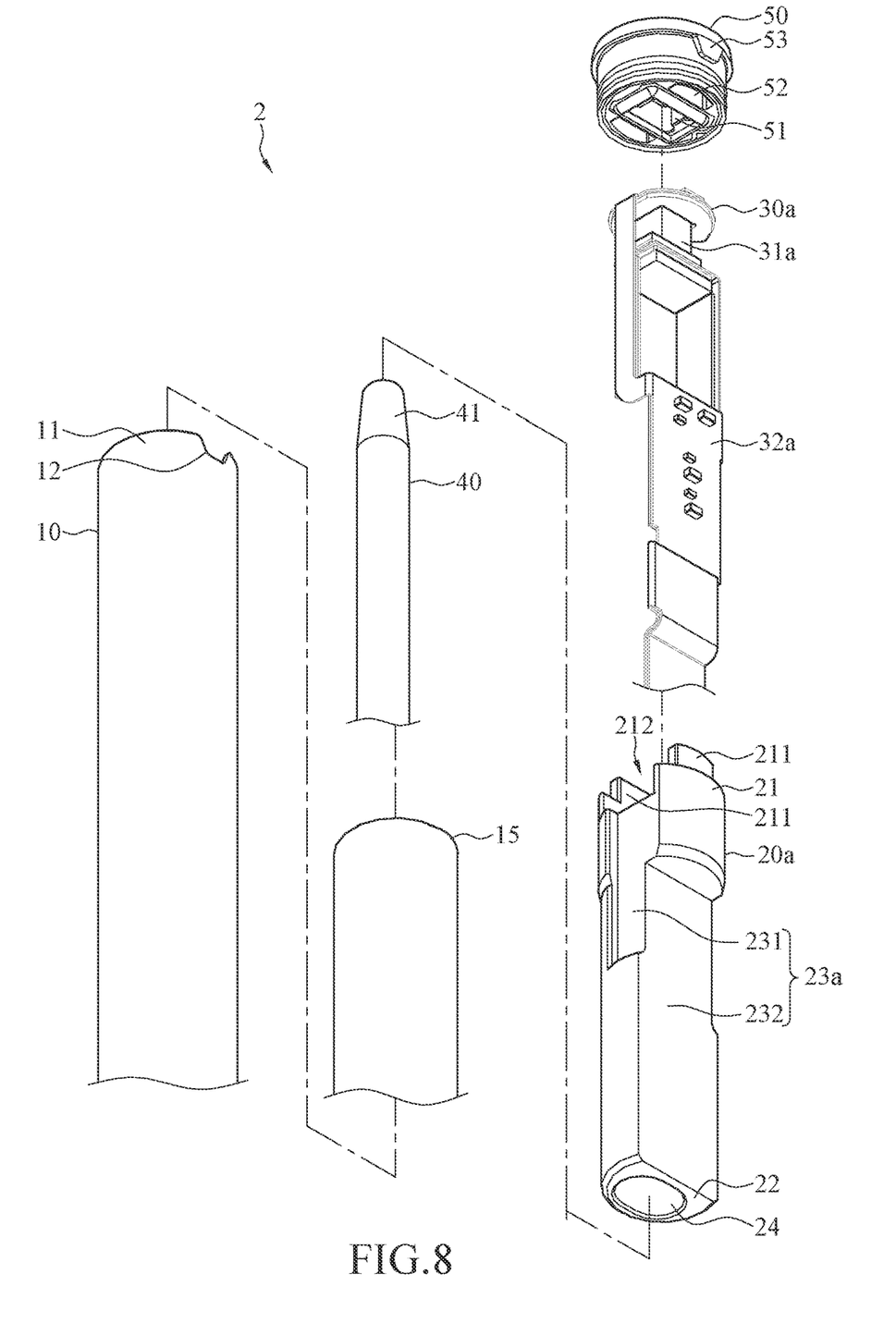
FIG. 8 illustrates an exploded view of an endoscope device according to a second embodiment of the instant disclosure.
Figure 9:
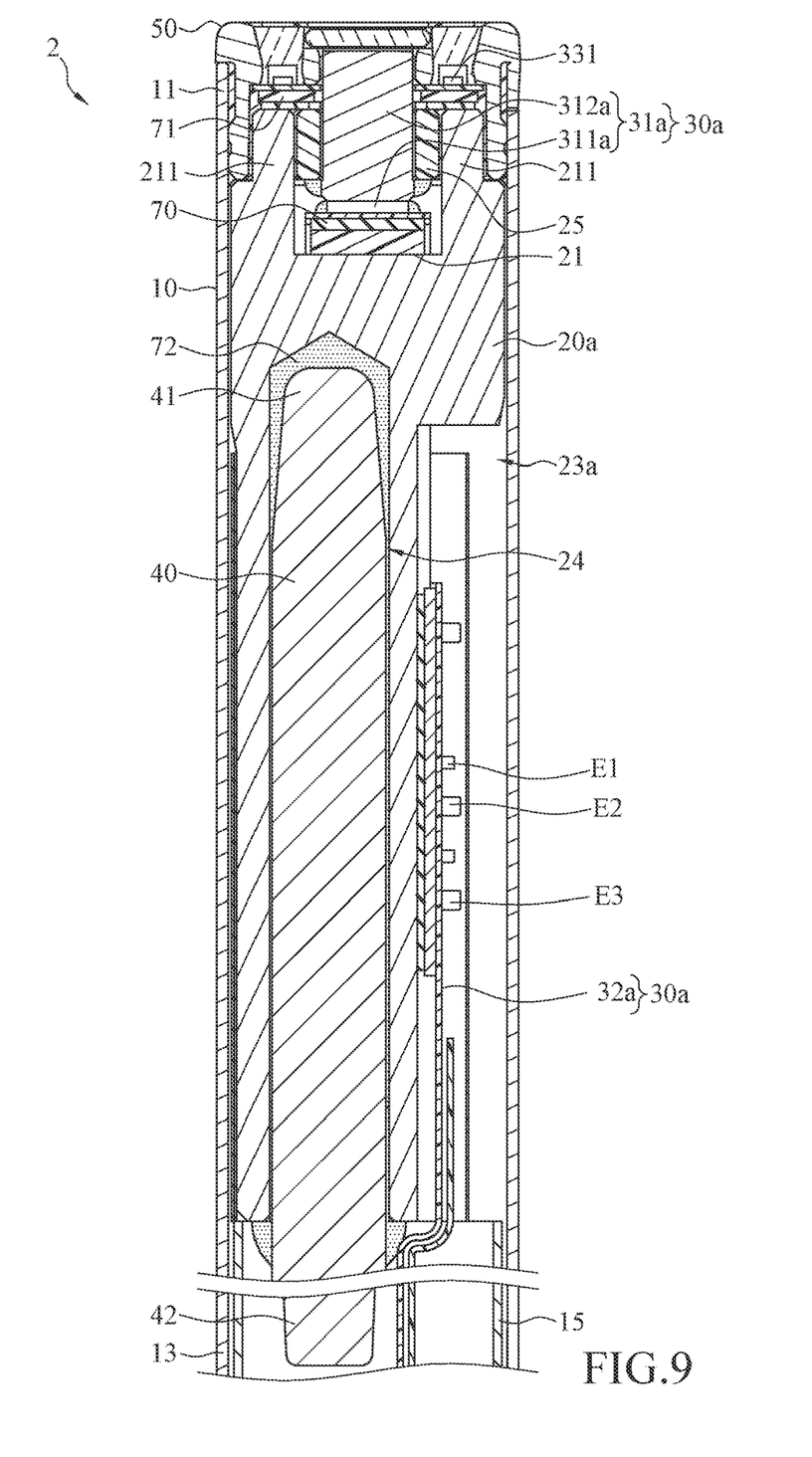
FIG. 9 illustrates a cross-sectional view of the endoscope device of the second embodiment.

As shown in FIGS. 8 and 9, which respectively illustrate an exploded view and a cross-sectional view of an endoscope device 2 according to a second embodiment of the instant disclosure. In the second embodiment, the receiving groove 23a of the thermal conductive member 20a of the endoscope device 2 comprises a first recess 231 and a second recess 232, and the first recess 231 and the second recess 232 are at different sides of the thermal conductive member 20a. In this embodiment, the first recess 231 and the second recess 232 are partially in communication with each other. The first recess 231 is in communication with the first end 21 of the thermal conductive member 20a, and the second recess 232 is in communication with the second end 22 of the thermal conductive member 20. In this embodiment, the camera module 31a of the image capturing module 30a comprises a single lens 311a and an optical sensing element 312a corresponding to the lens 311a. The circuit board 32a of the image capturing module 30a is received in the second recess 232. One of two ends of the circuit board 32a extends out of the first end 21 through the first recess 231 so as to be electrically connected to the image capturing module 30a, and the other end of the circuit board 32a extends out of the second end 22. Accordingly, the flexible feature of the circuit board 32a allows the circuit board 32a to be bent and disposed on the first recess 231 and the second recess 232, such that the space within the endoscope device 2 can be utilized more efficiently, thus allowing the thermal conductive member 20a to perform an optimized thermal conduction effect.

Further, as shown in FIGS. 8 and 9, in this embodiment, the camera module 31a of the image capturing module 30a only comprises one lens 311a, thus the overall size of the endoscope device 2 is reduced. Therefore, in this embodiment, a thermal conductive ring 25 may be further fitted over the lens 311a of the camera module 31a, and the thermal conductive ring 25 contacts the two thermal conductive posts 211 of the thermal conductive member 20a, so that the lens 311a indirectly contacts the two thermal conductive posts 211 through the thermal conductive ring 25. Therefore, the heat generated by the operation of the camera module 31a can be transmitted to the thermal conductive member 25. In some embodiments, the thermal conductive ring 25 may be a thermal conductive glue layer or a thermal conductive paste layer. In this embodiment, the heat between the thermal conductive member 20a and the lens 311a can be transmitted through the thermal conductive ring 25. Moreover, the thermal conductive ring 25 may be provided for positioning the thermal conductive member 20a and the lens 311a. Alternatively, the thermal conductive ring 25 may be a thermal conductive sheet or a thermal conductive silicon rubber so as to be sandwiched between the thermal conductive member 20a and the lens 311a, but embodiment are not limited thereto.

It should be noted that, same or similar elements in the endoscope device 1 of the first embodiment and in the endoscope device 2 of the second embodiment are represented by same reference numbers.

As above, according to the endoscope device of one or some embodiments of the instant disclosure, the thermal conductive member contacts the camera module and is provided for assembling and contacting the circuit board and the heat dissipation tube. Hence, the heat generated by operations of the camera module and the circuit board can be transmitted through the thermal conductive member and the heat dissipation tube, thus preventing from the condition that the human body is hurt by the excessive temperature of the inserted portion of the endoscope device, increasing the operation time of the endoscope device, and increasing lifetime of the electronic components in the endoscope device.

While the instant disclosure has been described by the way of example and in terms of the preferred embodiments, it is to be understood that the invention need not be limited to the disclosed embodiments. On the contrary, it is intended to cover various modifications and similar arrangements included within the spirit and scope of the appended claims, the scope of which should be accorded the broadest interpretation so as to encompass all such modifications and similar structures.

What is claimed is:

1. An endoscope device comprising:
    a hollow tube comprising an insertion end;
    a thermal conductive member disposed in the hollow tube and adjacent to the insertion end, wherein the thermal conductive member comprises a first end, a second end, and a receiving groove, the first end is near to the insertion end as compared with the second end, and the receiving groove is recessed from one side of the thermal conductive member and is in communication with the first end and the second end, where the thermal conductive member comprises an insertion groove, the insertion groove is at the second end;
    an image capturing module comprising a camera module and a circuit board, wherein the circuit board is received in the receiving groove and contacts the thermal conductive member, the camera module is disposed at the insertion end and electrically connected to the circuit board, the first end of the thermal conductive member contacts the camera module; and
    a heat dissipation tube disposed in the hollow tube, wherein one of two ends of the heat dissipation tube is inserted into the insertion groove and contacts the thermal conductive member, and the other end of the heat dissipation tube extends away from the insertion end, wherein
    the circuit board is a flexible circuit board and comprises a plurality of membrane circuit layers, the membrane circuit layers are extended from the first end to the second end of the thermal conductive member and stacked with each other, and the membrane circuit layers are respectively electrically connected to the camera module and a light emitting source.

2. The endoscope device according to claim 1, wherein the camera module comprises at least one lens and an optical sensing element, and the first end of the thermal conductive member contacts the optical sensing element.

3. The endoscope device according to claim 1, wherein the first end of the thermal conductive member indirectly contacts the camera module through a thermal conductive body.

4. The endoscope device according to claim 1, wherein the first end of the thermal conductive member further contacts the light emitting source.

5. The endoscope device according to claim 4, wherein the thermal conductive member indirectly contacts the light emitting source through a thermal conductive layer.

6. The endoscope device according to claim 4, wherein the first end of the thermal conductive member comprises two thermal conductive posts and a groove between the two thermal conductive posts, the camera module is received in the groove, and one of the two thermal conductive posts contacts the light emitting source.

7. The endoscope device according to claim 6, further comprising a cap assembled at the insertion end of the hollow tube, wherein the cap comprises a central assembling opening and at least one side assembling opening, the camera module is disposed at the central assembling opening, and the light emitting source is disposed at the at least one side assembling opening.

8. The endoscope device according to claim 7, wherein the cap has a first aligning portion, the insertion end of the hollow tube has a second aligning portion, and the first aligning portion corresponds to the second aligning portion.

9. The endoscope device according to claim 1, further comprising a thermal conductive ring, wherein the thermal conductive ring is fitted over the camera module and contacts the thermal conductive member.

10. The endoscope device according to claim 1, wherein the heat dissipation tube comprises a vaporization end and a condensation end, and the vaporization end of the heat dissipation tube is inserted into the insertion groove.

11. The endoscope device according to claim 1, wherein the hollow tube comprises an operation end opposite to the insertion end, and a handle is assembled with the operation end.

12. The endoscope device according to claim 11, wherein the handle has a first aligning member, the operation end of the hollow tube has a second aligning member, and the first aligning member corresponds to the second aligning member.

13. The endoscope device according to claim 11, wherein the handle comprises a mark portion, and the mark portion corresponds to an image capturing direction of the image capturing module.

14. The endoscope device according to claim 13, wherein the mark portion is a pattern.

15. The endoscope device according to claim 13, wherein the mark portion is a surface texture.

16. The endoscope device according to claim 1, further comprising an insulation tube disposed in the hollow tube, wherein at least one portion of the heat dissipation tube is located in the insulation tube.

* * * * *